(12) United States Patent
Labrecque

(10) Patent No.: US 11,666,256 B2
(45) Date of Patent: Jun. 6, 2023

(54) PULSE OXIMETER SENSOR

(71) Applicant: Michael Edward Labrecque, Las Cruces, NM (US)

(72) Inventor: Michael Edward Labrecque, Las Cruces, NM (US)

( * ) Notice: Subject to any disclaimer, the term of this patent is extended or adjusted under 35 U.S.C. 154(b) by 101 days.

(21) Appl. No.: 17/300,037

(22) Filed: Feb. 19, 2021

(65) Prior Publication Data

US 2022/0125353 A1 Apr. 28, 2022

Related U.S. Application Data

(60) Provisional application No. 63/204,819, filed on Oct. 27, 2020.

(51) Int. Cl.
*A61B 5/145* (2006.01)
*A61B 5/00* (2006.01)

(52) U.S. Cl.
CPC ........ *A61B 5/14542* (2013.01); *A61B 5/0004* (2013.01); *A61B 5/6816* (2013.01); *A61B 5/6838* (2013.01); *A61B 5/6898* (2013.01); *A61B 2560/0214* (2013.01)

(58) Field of Classification Search
CPC . A61B 5/14542; A61B 5/0004; A61B 5/6816; A61B 5/6838; A61B 5/6898; A61B 2560/0214; A61B 5/14552; A61B 5/01; A61B 5/021; A61B 2562/0219; A61B 2562/0233; A61B 5/02416; H04R 1/105
See application file for complete search history.

(56) References Cited

U.S. PATENT DOCUMENTS

| | | | |
|---|---|---|---|
| 5,611,337 A | 3/1997 | Bukta | |
| 5,729,615 A * | 3/1998 | Yang | H04R 1/1066 181/129 |
| 8,761,852 B2 | 6/2014 | Parthasarathy et al. | |
| 9,107,626 B2 | 8/2015 | Al-Ali et al. | |
| 9,138,181 B2 | 9/2015 | Haisley | |
| 9,320,885 B2 | 4/2016 | Vasapollo | |
| 9,515,417 B2 | 12/2016 | Fries et al. | |
| 10,413,197 B2 | 9/2019 | LeBoeuf | |
| 2004/0054291 A1 | 3/2004 | Schulz | |
| 2005/0033131 A1 | 2/2005 | Chen | |
| 2005/0197548 A1 | 9/2005 | Dietiker | |
| 2007/0032713 A1 | 2/2007 | Eghbal | |
| 2007/0038050 A1 | 2/2007 | Sarussi | |
| 2007/0073126 A1 | 3/2007 | Raridan | |
| 2007/0260131 A1 | 11/2007 | Chin | |
| 2007/0291953 A1 | 12/2007 | Ngla | |
| 2008/0146890 A1 * | 6/2008 | LeBoeuf | A61N 1/325 600/300 |
| 2009/0163775 A1 | 6/2009 | Barrett | |
| 2009/0163787 A1 | 6/2009 | Mannheimer | |

(Continued)

OTHER PUBLICATIONS

BCI Reusable Ear SpO2 Sensor.
Masimo 1863 LNCS DCI SpO2 Sensor.

*Primary Examiner* — Eric F Winakur
*Assistant Examiner* — Abid A Mustansir
(74) *Attorney, Agent, or Firm* — R. Wayane Pritchard

(57) ABSTRACT

A pulse oximeter sensor with earhook assembly for placement along the outside of a person's ear supported by the ear flap and ear lobe into which is placed a sensors for receiving and transmitting human body's analytics such as pulse or blood oxygen saturation.

12 Claims, 3 Drawing Sheets

(56) References Cited

U.S. PATENT DOCUMENTS

| | | |
|---|---|---|
| 2009/0171224 A1 | 7/2009 | Jochim |
| 2010/0081900 A1 | 4/2010 | Price |
| 2010/0081902 A1 | 4/2010 | McKenna |
| 2010/0331631 A1 | 12/2010 | MacLaughlin |
| 2011/0213274 A1 | 9/2011 | Telfort |
| 2012/0053430 A1 | 3/2012 | Flagler |
| 2012/0059267 A1* | 3/2012 | Lamego ............... A61B 5/021 600/483 |
| 2012/0216335 A1 | 8/2012 | McKenna |
| 2012/0253148 A1 | 10/2012 | Haisley |
| 2012/0253152 A1 | 10/2012 | Haisley |
| 2012/0253159 A1 | 10/2012 | Medina |
| 2012/0310061 A1 | 12/2012 | Al-Ali |
| 2013/0303864 A1 | 11/2013 | Chen |
| 2014/0031653 A1 | 1/2014 | Baker, Jr. |
| 2014/0058230 A1 | 2/2014 | Abdul-Hafiz et al. |
| 2014/0213864 A1 | 7/2014 | Abdul-Hafiz et al. |
| 2014/0275873 A1 | 9/2014 | Fries et al. |
| 2014/0288447 A1 | 9/2014 | Luna |
| 2015/0112169 A1 | 4/2015 | Lamego |
| 2016/0100780 A1 | 4/2016 | Vastola et al. |
| 2016/0361003 A1* | 12/2016 | Lange ................... A61B 5/681 |
| 2017/0224216 A1 | 8/2017 | Sampath et al. |
| 2017/0258403 A1 | 9/2017 | Abdul-Hafiz et al. |
| 2017/0325742 A1 | 11/2017 | Prior et al. |
| 2018/0020976 A1 | 1/2018 | Yossi |
| 2018/0055203 A1 | 3/2018 | Sandanger |
| 2018/0146897 A1 | 5/2018 | Baker, Jr. |
| 2018/0199869 A1 | 7/2018 | Huiku et al. |
| 2018/0214079 A1 | 8/2018 | Banet et al. |
| 2018/0318582 A1 | 11/2018 | Lee et al. |
| 2018/0348863 A1 | 12/2018 | Aimone |
| 2019/0022372 A1 | 1/2019 | Dar et al. |
| 2019/0038143 A1 | 2/2019 | Al-Ali |
| 2019/0060733 A1 | 2/2019 | Benson et al. |
| 2019/0117140 A1 | 4/2019 | Al-Ali et al. |
| 2019/0142344 A1 | 5/2019 | Telfort et al. |
| 2019/0212198 A1 | 7/2019 | Marsh |
| 2019/0216379 A1 | 7/2019 | Al-Ali et al. |
| 2020/0053463 A1* | 2/2020 | Daley .................. H04R 1/1066 |
| 2020/0280789 A1* | 9/2020 | Schrader ............... H04R 1/105 |

\* cited by examiner

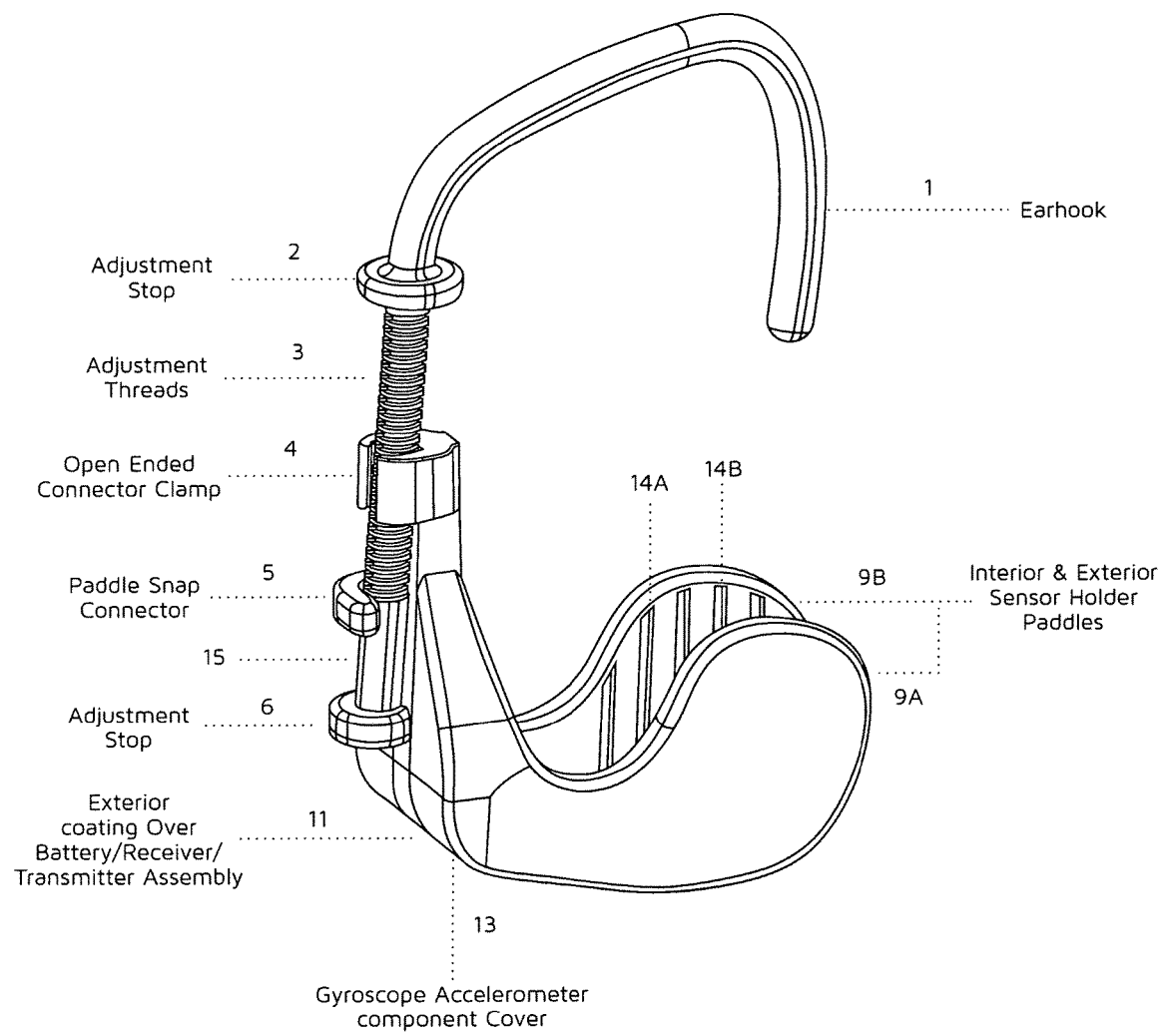
Fig. 3 OXY-FIT PLUS PULSE OXIMETER SENSOR

PULSE OXIMETER SENSOR

PROVISIONAL PRIORITY DATE

This application claims the benefit of an earlier filed provisional application, filed Oct. 27, 2020, Application Ser. No. 63/204,819.

BACKGROUND OF THE INVENTION

1. Field of the Invention

This invention relates to a pulse oximeter sensor.

2. Description of the Prior Art

Assemblies used to allow placement of devices next to a person's ear such as ear buds for listening to music are prevalent throughout modern culture. In the medical field, these assemblies allow receiving and transmission human body analytics such as pulse rate or blood oxygen saturation. Sensors used to gather medical information from a patient are fixed to a patient's ear using one of two methods; ones that fit within the ear canal and ones that are placed on the ear using the earlobe. US Patent Application 2004/0054291, Inventor Christian Schulze, et al, for Pulse Oximetry Ear Sensor, is an example of an earhook assembly in the medical field wherein the assembly is placed on the outside of the ear along the ear flap and earlobe. US Patent Application 2005/0033131, Inventor Yunqunn Chen, et al, for Ear Sensor Assembly and US Patent Application 2014/0288447, Inventor Michael Edward Smith Luna, et al, for Ear Related Devices Implementing Sensors to Acquire Physiological Characteristics, are examples of assemblies that are placed into the ear canal. What all these examples have in common is that each is designed to house a permanent sensor. If the sensor fails, the earhook assembly is replaced. Additionally, these types of earhook assemblies generally result in an uncomfortable attachment to a person's ear for the reason that the sensors employed require tighter earlobe support resulting in a pinching of the ear lobe or are uncomfortable because they are placed into a person's ear canal.

Clearly it can be appreciated in the art that a single piece, ergonomic ear hook assembly with either a wired or wireless transmission of valuable health data from sensors to a receiver would be desired both from a cost as well as a ease of use approach.

SUMMARY OF THE INVENTION

It is, therefore, an object of the present invention to provide a pulse oximeter sensor with ear attachment that will receive and transmit human body analytics. Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 3 is a side view of the present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 1:
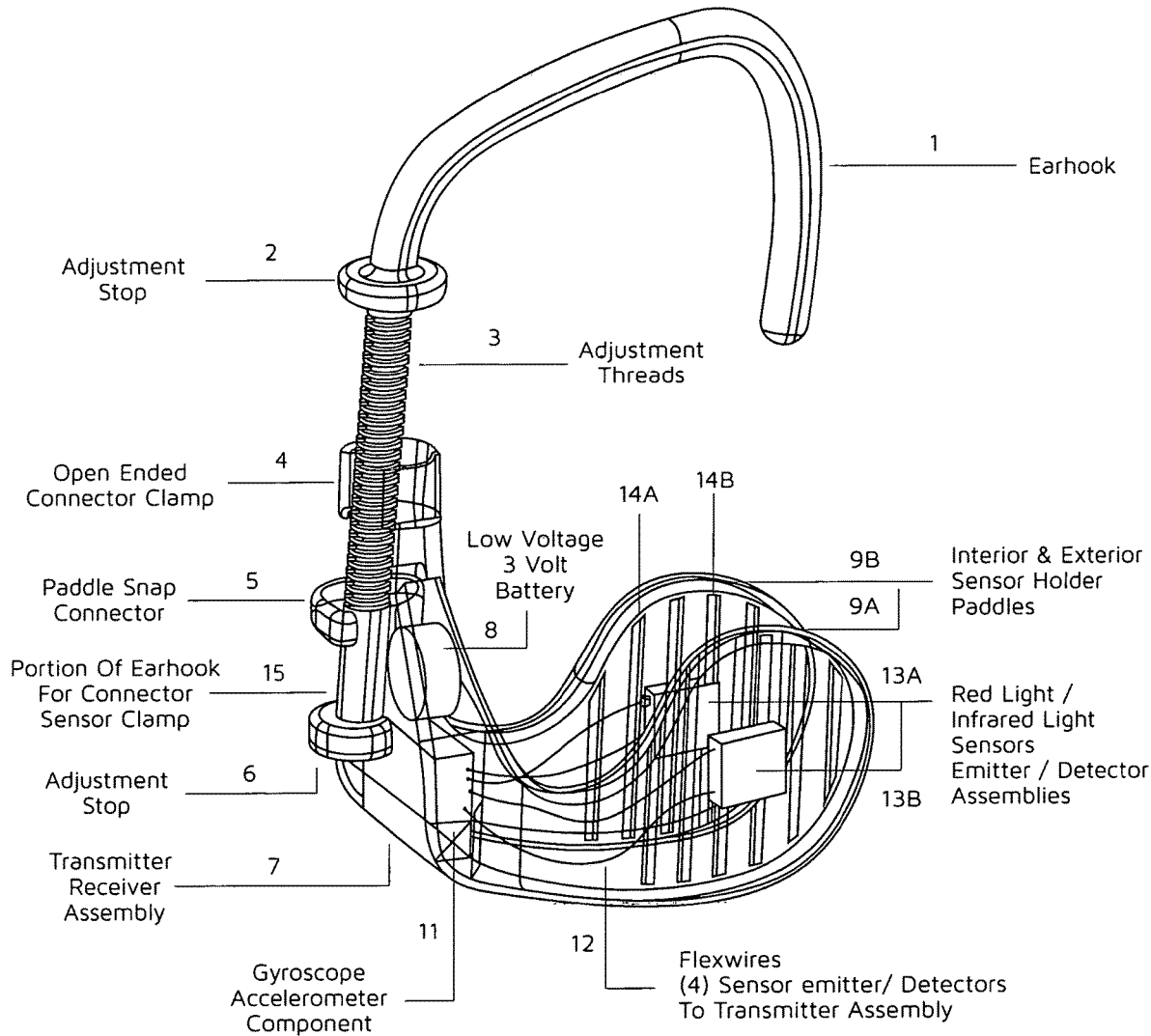
FIG. 1 is a side view of the present invention.
Figure 2:
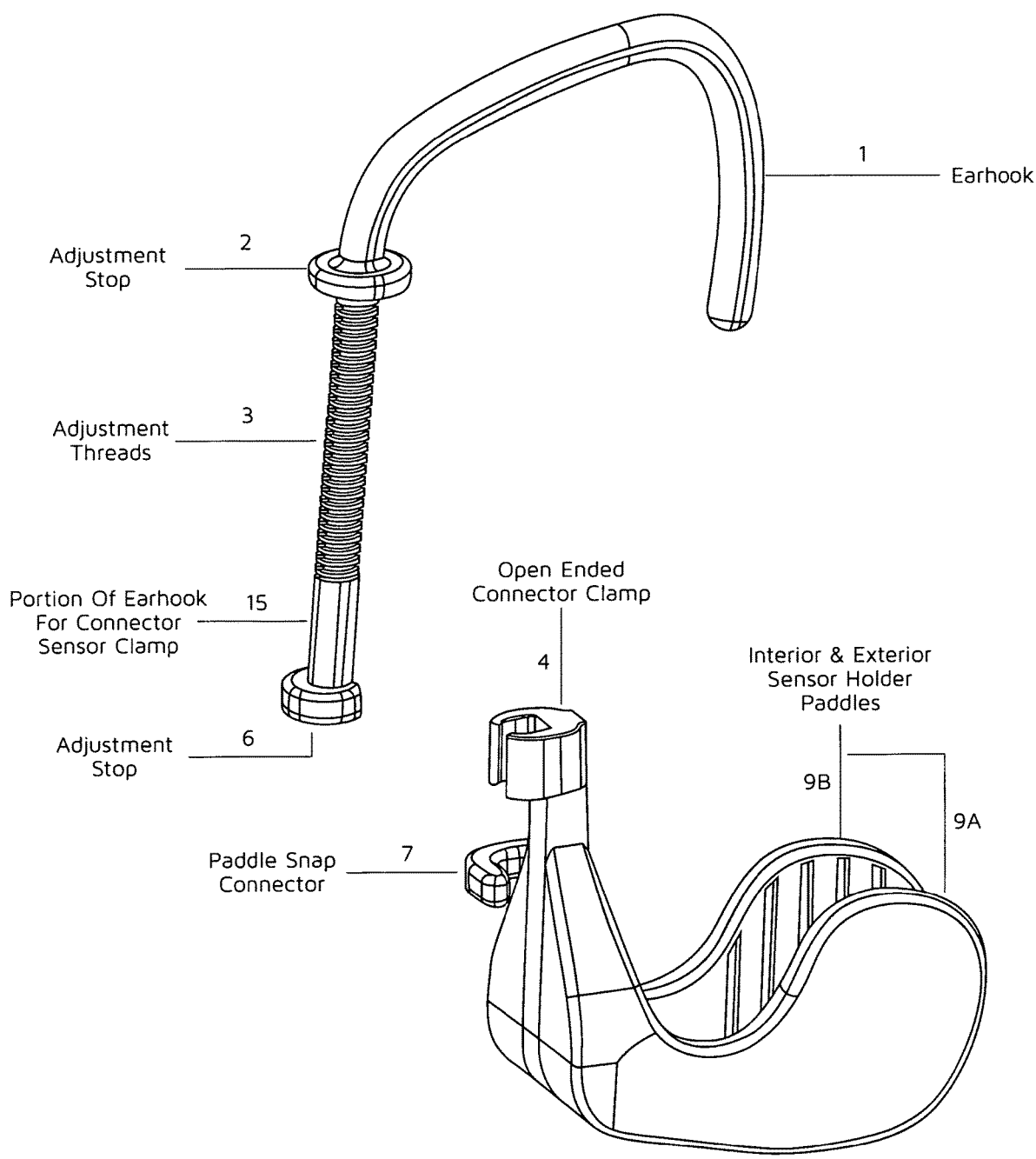
FIG. 2 depicts a side view of the present invention with ear hook detached from the sensor holder.

The pulse oximeter sensor assembly of the present invention, depicted in FIGS. 1, 2 and 3, is made from any material of sufficient rigidity, flexibility and strength to be supported by the ergonomically designed earhook [1] along the top, inside edge of a person's upper ear. The earhook [1] is securely attached to an adjustment device comprising adjustment threads [3], a non-threaded portion [11] and adjustment stops [2 and 6]. Depicted in FIGS. 1, 2 and 3 is the earlobe assembly comprising sensor holder paddles [9A and 9B] which fit along the outside of the inner and outer earlobe. Although the earlobe assembly of the present invention is attached to the earhook [1] using at least two connector clamps shown in FIGS. 1, 2 and 3 as paddle snap connector [5] and open ended connector clamp [4], more than 2 connector clamps could be used. The adjustment threads [3] mate with and rotate through the open ended connector clamp [4]. As the threaded component [7] is rotated, the sensor holder paddles [9A and 9B] will move up or down on the adjustment threads [3] depending on the direction of the rotation. The paddle snap connector while not threaded, will travel up or down the non-threaded portion [15] in conjunction with movement of the adjustment threads [3] through the open ended connector clamp [4]. This movement allows adjustment of the earhook [1] to better fit a person's ear.

Although FIGS. 1, 2, and 3 illustrate a pulse oximeter sensor that transmits medical information of a patient using a wireless transmitter receiver [7] the transmitter could also be wired to a receiver. The pulse oximeter sensor must include a power source which is shown in FIGS. 1, 2 and 3 as a battery [8]. Other sources of power could also be used such as a hard wire connection to an electrical power source.

As shown in FIGS. 1, 2 and 3, the inside surfaces [14A and 14B] of the sensor holder paddles [9A and 9B] can be textured to form a more secure attachment. FIG. 2 illustrates that the inside surfaces [14A and 14B] of the sensor holder paddles [9A and 9B] include sensors [13A and 13B] for receiving and transmitting human body analytics such as movement (gyroscopic component), pulse and/or blood oxygen content. While two sensors [13A and 13B] are shown in FIG. 2, more than 2 sensor could be utilized depending on the need and function desired. Other body analytics can be measured using the sensors such as temperature and blood pressure depending on the type of sensor used. Information from sensors [13A and 13B] is transmitted from such sensors to the transmitter receiver assembly [7]. Transmission can be through wires [12] shown in FIGS. 1, 2, and 3 or wireless technology utilizing methods such as bluetooth or WIFI.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A pulse oximeter sensor comprising an earhook ergonomically designed to fit along the top, inside edge of a person's ear flap; an adjustment device secured to the earhook, the adjustment device including adjustment threads; an earlobe assembly removably secured to the adjustment threads, the earlobe assembly comprising two sensor holder paddles rotatably attached to the adjustment threads, wherein the two sensor holder paddles are designed to fit on the inside and outside surfaces of a person's ear lobe; sensors which are configured to contact the inside and outside surfaces of a person's ear lobe located on the surface of each sensor holder paddle in contact with a person's ear lobe; an electrical power source; and a transmitter receiver assembly to which human body analytic information from the sensors is transmitted.

2. The pulse oximeter sensor of claim 1 wherein the transmitter receiver assembly is further configured to transmit the human body analytic information to a secondary receiver.

3. The pulse oximeter sensor of claim 1 wherein the human body analytic information is transmitted wirelessly from the sensors to the transmitter receiver assembly and then to a secondary receiver.

4. The pulse oximeter sensor of claim 3 wherein the secondary receiver is a smart phone capable of utilizing the human body analytic information.

5. The pulse oximeter sensor of claim 1 wherein the electrical power source is a battery attached to the pulse oximeter sensor.

6. The pulse oximeter sensor of claim 1, wherein the ear lobe assembly includes a paddle snap connector and an open ended connector clamp, the adjustment threads mate with and rotate through the open ended connector clamp and the snap connector travels up and down the adjustment device.

7. A pulse oximeter sensor comprising an earhook ergonomically designed to fit along the top, inside edge of a person's ear flap; an adjustment device secured to the earhook, the adjustment device including adjustment threads with stop fittings with a non-threaded component; an earlobe assembly removably secured to the adjustment device, the earlobe assembly comprising an open ended connector clamp which is secured to and rotates along the adjustment threads, a paddle snap connector which slides up and down the non-threaded component, two sensor holder paddles which are configured to fit on the inside and outside surfaces of a person's ear lobe, and sensors which contact the inside and outside surfaces of a person's ear lobe located on the surface of each sensor holder paddles in contact with a person's ear lobe; an electrical power source; and a transmitter receiver assembly to which human body analytic information from the sensors is transmitted.

8. The pulse oximeter sensor of claim 7 wherein the transmitter receiver assembly is further configured to transmit the human body analytic information to a secondary receiver.

9. The pulse oximeter sensor of claim 7 wherein the human body analytic information is transmitted wirelessly from the sensors to, the transmitter receiver assembly and then to a secondary receiver.

10. The pulse oximeter sensor of claim 9 wherein the secondary receiver is a smart phone capable of utilizing the human body analytic information.

11. The pulse oximeter sensor of claim 7 wherein the electrical power source is a battery attached to the pulse oximeter sensor.

12. The pulse oximeter sensor of claim 7, wherein the ear lobe assembly includes a paddle snap connector and an open ended connector clamp, the adjustment threads mate with and rotate through the open ended connector clamp and the snap connector travels up and down the adjustment device.

* * * * *